United States Patent [19]
Davidson et al.

[11] Patent Number: 5,509,933
[45] Date of Patent: Apr. 23, 1996

[54] MEDICAL IMPLANTS OF HOT WORKED, HIGH STRENGTH, BIOCOMPATIBLE, LOW MODULUS TITANIUM ALLOYS

[75] Inventors: James A. Davidson, Germantown; Ajit K. Mishra, Memphis, both of Tenn.

[73] Assignee: Smith & Nephew Richards, Inc., Memphis, Tenn.

[21] Appl. No.: 36,414

[22] Filed: Mar. 24, 1993

Related U.S. Application Data

[63] Continuation-in-part of Ser. No. 986,280, Dec. 7, 1992, abandoned, which is a continuation-in-part of Ser. No. 647,453, Jan. 28, 1991, Pat. No. 5,169,597, which is a continuation of Ser. No. 454,181, Dec. 21, 1989, abandoned.

[51] Int. Cl.$^6$ ............... A61F 2/28; A61F 5/00; A61F 2/36
[52] U.S. Cl. ............... 623/16; 623/18; 623/23; 606/72; 606/60; 606/69
[58] Field of Search ............... 623/11, 16, 18, 623/66, 20, 22; 606/53, 69, 76; 148/421, 669

[56] References Cited

U.S. PATENT DOCUMENTS

| | | | |
|---|---|---|---|
| 2,892,706 | 4/1959 | Jaffee et al. | |
| 2,987,352 | 5/1961 | Watson | |
| 3,370,946 | 1/1968 | Bertea et al. | |
| 3,643,658 | 2/1972 | Steinemann | |
| 3,677,795 | 7/1972 | Bokros et al. | |
| 3,752,664 | 8/1974 | Steinemann | 420/417 |
| 3,777,346 | 12/1973 | Steinemann | |
| 3,849,124 | 11/1974 | Villani | 420/417 |
| 3,911,783 | 10/1975 | Gapp et al. | 420/417 |
| 4,040,129 | 8/1977 | Steinemann et al. | 623/16 X |
| 4,145,764 | 3/1979 | Suzuki et al. | |
| 4,170,990 | 10/1979 | Baumgart et al. | 606/78 |
| 4,197,643 | 4/1980 | Burstone et al. | 420/421 |
| 4,511,411 | 4/1985 | Brunner et al. | |
| 4,857,269 | 8/1989 | Wang et al. | 420/417 |
| 4,902,359 | 2/1990 | Takeuchi et al. | 148/133 |
| 4,983,184 | 1/1991 | Steinemann | 623/66 |
| 5,169,597 | 12/1992 | Davidson et al. | 428/613 |

FOREIGN PATENT DOCUMENTS 2703529  8/1978  Germany.

OTHER PUBLICATIONS

Zwicker, et al., Z. Metallkunde, 61 (1970) pp. 836–847.
Collins (ed), "A Sourcebook of Titanium Alloy Superconductivity," Plenum, N.Y. 1983, pp. 342, 352, 357, 358, 366, 405–412, 418–419.
Albert, et al., Z. Metallunde, 63 (1972) 126.
Brown & Merritt, "Evaluation of Corrosion Resistance of Biology," Case Western Reserve University, 13 Feb. 1986 (1:8).
Mears, "Electron–Probe Microanalysis of Tissue and Cells from Implant Areas," JNL of Bone and Joint Surgery, vol. 48B, No. 3, pp. 567–576 (Aug. 1966).

(List continued on next page.)

Primary Examiner—David Isabella
Attorney, Agent, or Firm—Pravel, Hewitt, Kimball & Krieger

[57] ABSTRACT

Biocompatible medical implants from a high strength, low modulus, hot worked titanium alloy containing titanium, about 10–20 wt. % or 35 to about 50 wt. % niobium and up to 20 wt. % zirconium. In particular, the titanium implants have a modulus of elasticity closer to that of bone than other typically used metal alloys and does not include any elements which have been shown or suggested as having short or long term potential adverse effects from a standpoint of biocompatibility. To fabricate the alloy, it is necessary to heat to above the β-transus temperature (or to a temperature in a range from 100° C. below and up to the β-transus), hot work the alloy, rapidly cool to below the β-transus, and age the cooled alloy for a period of time to develop its strength while maintaining its low modulus (less than about 90 GPa). The alloy is suitable for a range of uses where the properties of low modulus, high strength and corrosion resistance are desirable.

40 Claims, 6 Drawing Sheets

OTHER PUBLICATIONS

Ferguson, Laing, and Hodge, "The Ionization of Metal Implants in Living Tissues," JNL of Bone and Joint Surgery, vol. 42A, No. 1, pp. 77–90 (Jan. 1960).

Hoar and Mears, "Corrosion–Resistant Alloys in Chloride Solutions: Materials for Surgical Implants," pp. 506–507.

Kirk–Othmer Encyclopedia of Chemical Technology, vol. 23, pp. 98–113.

Collins, "Physical Metallurgy of Titanium Alloys," American Society for Metals Series in Metal Processing.

Jepson, et al., The Science & Tech., Titanium Ed. Jaffee, et al., Pergamon, N.Y. 1968, p. 677.

Heller, et al., Jour. Less Common Metals, 24 (1971) 265.

Van Noort, R., Jour. Mat. Sci., 22 (1987) 3801.

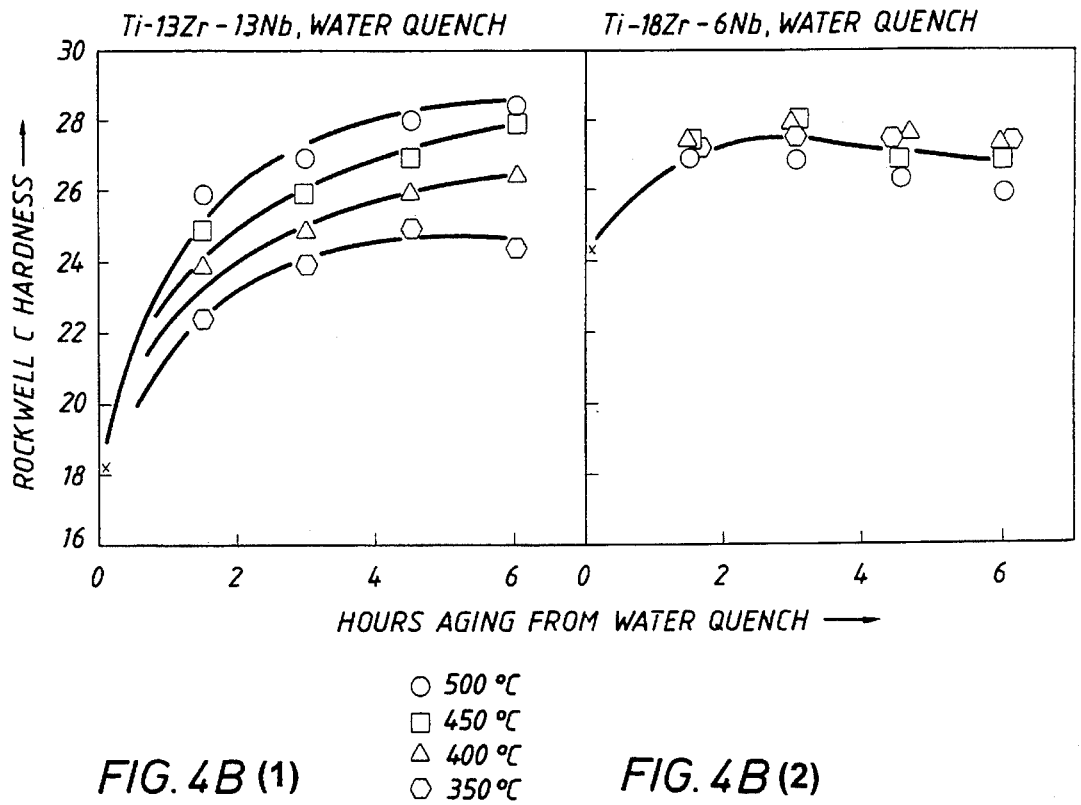
FIG. 4A (1) Ti-13Zr-13Nb, WATER QUENCH
FIG. 4A (2) Ti-18Zr-6Nb, WATER QUENCH
HOURS AGING FROM WATER QUENCH
○ 500 °C
□ 450 °C
△ 400 °C
⬠ 350 °C
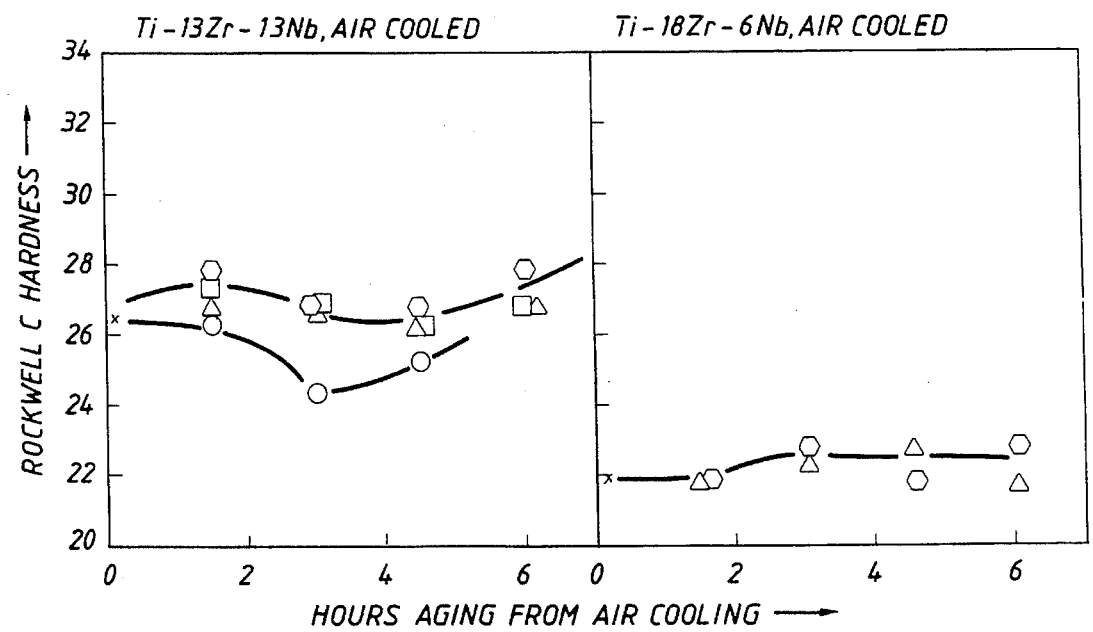
FIG. 4B (1) Ti-13Zr-13Nb, AIR COOLED
FIG. 4B (2) Ti-18Zr-6Nb, AIR COOLED
HOURS AGING FROM AIR COOLING FIG. 5A
FIG. 5B
FIG. 6A
FIG. 7
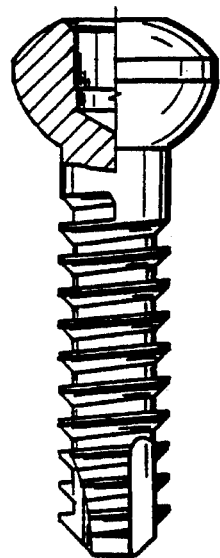
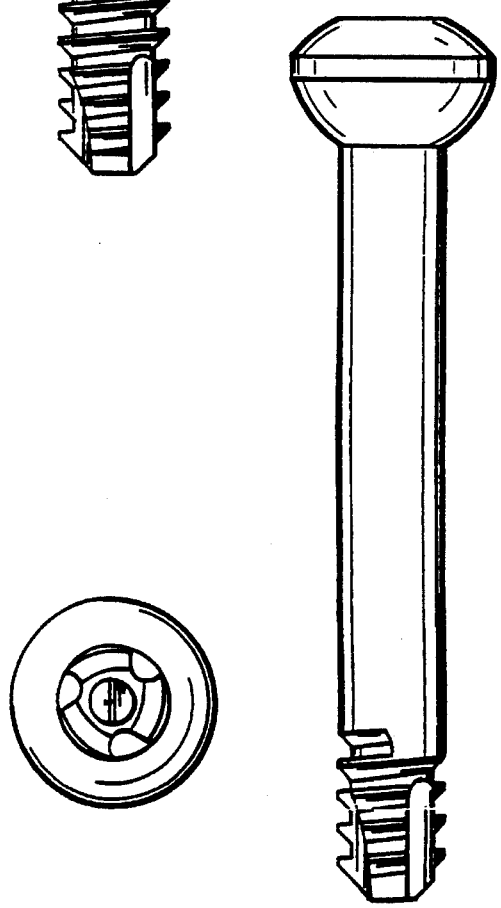
FIG. 6B FIG. 8
FIG. 9A
FIG. 9B
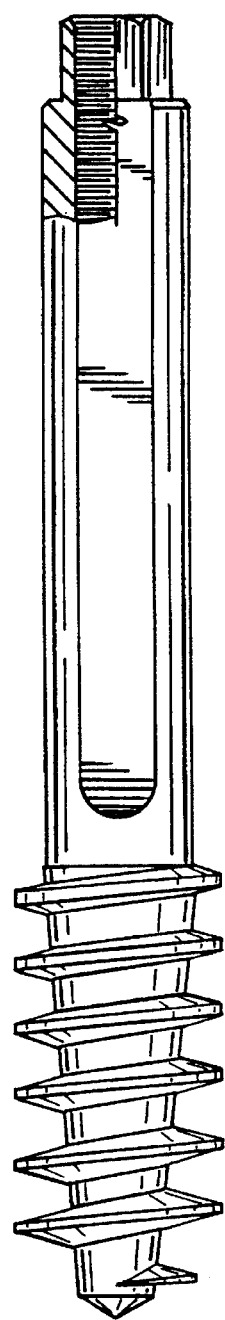
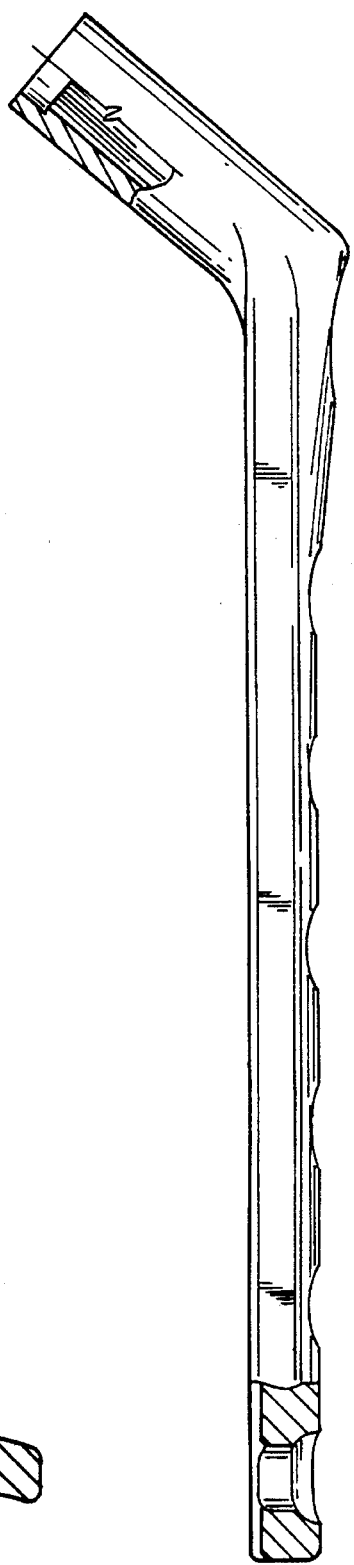
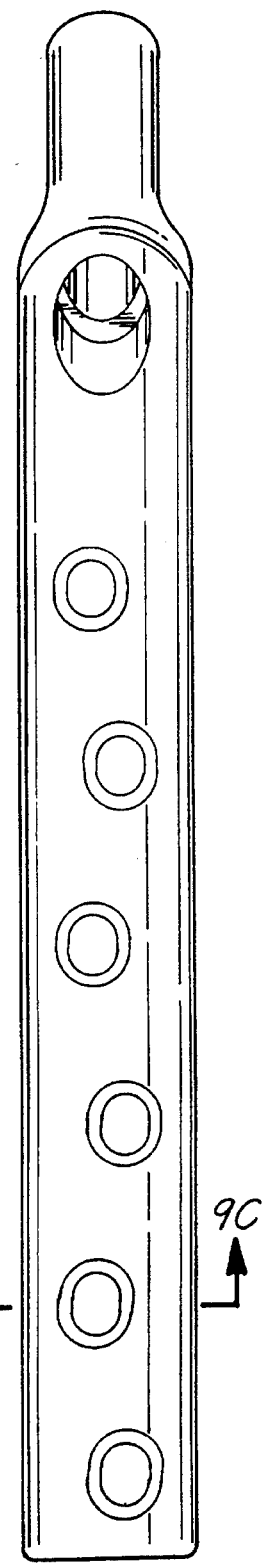
FIG. 9C

MEDICAL IMPLANTS OF HOT WORKED, HIGH STRENGTH, BIOCOMPATIBLE, LOW MODULUS TITANIUM ALLOYS

RELATED APPLICATIONS

This application is a continuation-in-part of U.S. Ser. No. 07/986,280, filed on Dec. 7, 1992, now abandoned, which is in turn a continuation-in-part of Ser. No. 647,453, now U.S. Pat. No. 5,169,597, issued Dec. 8, 1992, which is in turn a continuation of U.S. Ser. No. 07/454,181 filed Dec. 21, 1989, now abandoned.

BACKGROUND

1. Field of the Invention

This invention relates to high strength, biocompatible metallic implants. In particular, the invention is of titanium alloy medical implants that have a low modulus of elasticity and high strength produced by a series of specific metallurgical steps to which the alloy is subjected. Further, the alloy does not include any elements which have been shown or suggested as having short term or long term potential adverse effects when implanted in the human body.

2. Background of the Invention

For many applications there has been, and there continues to be, a need for a metal that has a low modulus of elasticity but is also strong, fatigue-resistant, corrosion resistant, and has a hard surface that is resistant to abrasive wear. For instance, in the orthopedic implant art, metals are still the most commonly used material for fabricating load-bearing implants such as, for instance, hip joints and knee joints.

Metals and metal alloys such as stainless steel, vitalium (cobalt alloy) and titanium have been used successfully. These materials have the requisite strength characteristics but typically have not been resilient or flexible enough to form an optimum implant material. Also, many alloys contain elements such as aluminum, vanadium, cobalt, nickel, molybdenum, and chromium which recent studies have suggested might have some long term adverse effects on human patients.

Many of the metal alloys typically used in prosthetic implants were developed for other applications, such as Ti—6Al—4V alloy in the aircraft industry. These alloys were later thought to be suitable for use as implant materials because they possess mechanical strength and appeared to have acceptable levels of biocompatibility. However, these metals typically have elastic moduli much higher than that of bone, for example, 316 stainless steel has an elastic modulus of about 200 GPa while that of cast heat-treated Co—Cr—Mo alloy is about 240 GPa. Of these, the alloy with the lowest elastic modulus is Ti—6Al—4V with an elastic modulus of about 120 GPa.

It has also been found that many of these metals will corrode to some extent in body fluids thereby releasing ions that might possibly be harmful over a prolonged period of time. It is now believed that the corrosive effects of body fluids is due both to chemical and electro-chemical processes, with corrosion products forming when certain commonly-used metal alloys ionize from corrosion processes in the body. For example, aluminum metal ions have been associated with Alzheimer's disease and vanadium, cobalt, molybdenum, nickel and chromium are suspected of being toxic or carcinogenic.

It has been suggested that metals could be coated with a biocompatible plastic, ceramic or oxide to overcome the corrosion problem. However, coatings tend to wear off, especially on articulating bearing surfaces of total joints, and are susceptible to delaminating and separating from the metal substrate, exposing the metal to body fluids.

Generally, it is the industry practice to passivate the implant metal alloys. However, passivation produces only thin, amorphous, poorly attached protective oxide films which have not proved totally effective in eliminating the formation of corrosion products in the body, particularly in situations where fretting occurs in the body.

As implant metals, titanium alloys offer advantages over stainless steels because of their lower susceptibility to corrosion in the body coupled with their high strength and relatively low modulus of elasticity. Upon cooling, the currently used Ti—6Al—4V alloy transforms from a $\beta$-structure to an $\alpha$ plus $\beta$ structure at about 1000° C. This transition can be shifted to a lower temperature by the addition of one or more suitable $\beta$-phase stabilizers such as molybdenum, zirconium, niobium, vanadium, tantalum, cobalt, chromium, iron, manganese and nickel.

Some efforts have been directed toward the development of alloys that eliminate harmful metals. For example, U.S. Pat. No. 4,040,129 to Steinemann et al. is directed to an alloy which includes titanium or zirconium as one component and, as a second component, any one or more of: nickel, tantalum, chromium, molybdenum or aluminum, but does not recognize or suggest any advantages from having a relatively low elastic modulus, or advantages or disadvantages associated with high temperature sintering treatments (at about 1250° C.), commonly employed to attach porous metal coatings into which bone can grow to stabilize non-cemented, press-fit devices into the skeletal structure.

Although Steinemann provides that copper, cobalt, nickel, vanadium and tin should be excluded, apart from their presence as unavoidable impurities, the patent indicates that it is permissible to have any or all of chromium, molybdenum and aluminum, which are all believed to have potential long-term adverse effects, present in the alloy as long as their combined weight does not exceed 20% of the total weight of the alloy.

U.S. Pat. 4,857,269 to Wang et al. is not a statutory bar and its citation is not an admission that its teachings are applicable prior art. This patent relates to a titanium alloy for a prosthetic implant said to have high strength and a low modulus. The titanium alloy contains up to 24 wt. % of at least one isomorphous beta stabilizer from the group molybdenum, tantalum, zirconium and niobium; up to 3 wt. % of at least one eutectoid beta stabilizer from the group iron, manganese, chromium, cobalt or nickel; and optionally up to 3 wt. % of a metallic $\alpha$-stabilizer from the group aluminum and lanthanum. Incidental impurities up to 0.05% carbon, 0.30% oxygen, 0.02% nitrogen, and up to 0.02% of the eutectoid former hydrogen are also included. Although there is some discussion of having an elastic modulus (e.g., Young's modulus) around 85 GPa, the only examples of a low modulus (66.9–77.9 GPa) all contain 11.5 wt. % Mo which is a potentially toxic element and undesirable for optimizing biocompatibility.

Other currently used metal alloys have similar drawbacks. For example, the commonly used Ti—6Al—4V alloy, with appropriate heat treatment, offers some degree of biocompatibility but has an elastic modulus of about 120 GPa. Although this elastic modulus is lower than other alloys and accordingly offers better load transfer to the surrounding bone, this modulus is still significantly greater than desired. Moreover, the alloy contains aluminum and also vanadium, which is now suspected to be a toxic or carcinogenic material when present in sufficient quantity.

Commercially available PROTOSUL 100 (Sulzer Bros. Ltd.) is a Ti—6Al—7Nb alloy which intentionally avoids the potentially adverse effects of vanadium toxicity by substituting niobium. However, the alloy still contains aluminum and has an elastic modulus of about 110 GPa (15.9×10 psi) in heat-treated condition, and with a tensile strength of about 1060 MPa.

With orthopedic prostheses being implanted in younger people and remaining in the human body for longer periods of time, there is a need for an implant material with requisite strength and flexibility requirements, which does not contain elements which are suspected as having long-term harmful effects on the human body. Desirably, the implant material should have a hardened surface or coating that is resistant to microfretting wear and gross mechanical wear.

While the above discussion has concentrated largely on the area of medical prostheses, there also exists a need in other areas of technology for a metal that has low modulus and high strength, is corrosion resistant and may be hardened or coated with a hard coating material. For example, such a metal would find application in aircraft frames and cladding, automobile chassis and springs, bicycle frames, turbine blades and rotors, boat masts, submersible shell cladding and structural frames, boat hulls, golf clubs, tennis rackets and a host of other uses. Also, if the metal is corrosion resistant, then it would find application in mining extraction equipment used to handle acidic, corrosive slurries and down-well applications in oil wells where there exists a corrosive hot, acidic environment. Indeed, the potential commercial uses for a low modulus, high strength, corrosion resistant alloy are too numerous to recite.

SUMMARY OF THE INVENTION

The invention provides novel medical implants fabricated from hot worked, high strength, low modulus alloys of titanium, niobium and zirconium. The alloys are preferably free of toxic or potentially toxic compositions when used as an implant fabrication alloy. The hot worked alloys also find application in structural aircraft components, automobile components, bicycle frames, equipment used in corrosive conditions, and the like, where a corrosion resistant, high strength, low modulus metal is needed. More specifically, the invention alloy comprises titanium and niobium and optionally zirconium. To achieve the lowest modulus, the titanium should preferably be alloyed with from about 10 wt. % to about 20 wt. % niobium or from about 35 wt. % to about 50 wt. % niobium. Zirconium is an optional component preferably present in an amount from about 0 to about 20 wt. %. Most preferably the invention alloy comprises about 74 wt. % titanium, about 13 wt. % zirconium and about 13 wt. % niobium.

The invention alloy is strengthened by a hot working process wherein the alloy is heated to a temperature above its β-transus, or within about 100° C. below its β-transus, hot worked, and then cooled rapidly, following which it is aged at temperatures below the β-transus. Preferably, this aging is carried out for about 2 to about 8 hours, most preferably about 6 hours at about 500° C. The aging process may also consist of a gradual ramp-up from room temperature, preferably in about 0.5 to 10 hours, during which preaging of the material may occur, followed by isothermal aging at an appropriate temperature below the β-transus for from about 15 minutes to 20 hours, preferably about 6 hours. Note that by the time the alloy is removed from the furnace and the hot working operation performed, the temperature of the alloy may have decreased significantly; so the hot working operation may actually occur at a temperature significantly lower than the temperature to which the alloy is heated prior to hot working. The invention's hot worked, quenched and aged titanium alloys have a low elastic modulus (about 60 to about 90 GPa) and have tensile strengths exceeding about 700 MPa, preferably exceeding about 800 MPa.

Further, the invention implants may be surface hardened by any one of several processes used in the field of metallurgy but not necessarily known for use with medical implants. For example, there are processes in which the alloy is subjected to nitrogen or oxygen diffusion, internal oxidation, or nitrogen or oxygen ion implantation. A description of these techniques may be found in our copending application, U.S. Ser. No. 832,735, filed Feb. 7, 1992, which is hereby incorporated by reference as if fully set forth. Clearly, the alloy should be formed into the desired shape for its intended use before surface hardening or the benefits of surface hardness may be lost in any subsequent shaping operations that affect or remove the surface of the alloy to a significant extent. Further, the shaped alloy may be worked for strength enhancement before surface hardening.

The most preferred hot worked, low modulus, high strength alloy for making medical implants contains about 74 wt. % titanium, and about 13 wt. % each of zirconium and niobium. Other elements are not deliberately added, but may be present in trace amounts to the extent that they were present as unavoidable impurities in the metals used to produce the alloy. Other non-toxic filler materials such as tantalum, which could be used to stabilize the β-phase, but not affect the low modulus (i.e., maintain it less than about 90 GPa), could also be added. The exclusion of elements beside titanium, zirconium and niobium or tantalum results in an alloy which does not contain known toxins or carcinogens or elements that are known or suspected of inducing diseases or adverse tissue response in the long term. Such an alloy is particularly useful in medical implant applications.

The invention's hot worked, low modulus, high strength titanium implants are produced by heating to above the β-transus temperature (or within the range including those temperatures below and within less than about 100° C. of the β-transus temperature); hot working the implant; rapidly cooling the hot worked alloy to about room temperature; then reheating and aging at temperatures below the β-transus, in the range of 350°–550° C., preferably about 500° C., for a time sufficient to provide an implant of adequate strength.

In a particularly preferred aging process, the implant is preaged by gradually heating the quenched implant for a period of time up to about 350°–550° C. Thereafter, the preaged implant is isothermally aged at this temperature for a time sufficient to develop strength and hardness characteristics required.

The invention implants have a low modulus of elasticity of less than about 90 GPa. This is a significant improvement over Ti—6Al—4V which has a modulus of elasticity of about 120 GPa.

In certain applications it may still be desirable to coat the implant's surface with wear-resistant coatings such as amorphous diamond-like carbon coatings, zirconium dioxide coatings, titanium nitrides, carbides, or the like for protection against potential micro-fretting wear such as might occur on the bearing surfaces of implant prostheses.

A porous coating, such as a bead, powder, or wire mesh coating, as exemplified schematically in FIG. 1 as 10 on hip stem prosthesis 12, may be applied to implants of many types for a variety of applications fabricated from the inventive alloy. Such coatings are often useful to provide interstitial spaces for bone or tissue ingrowth into the implant, which tends to stabilize the implant in the skeletal structure.

While implants fabricated from the invention hot worked alloy possess high strength, the usefulness of these prostheses is not limited to load-bearing applications. Because of its corrosion resistance, non-toxicity and relatively low modulus of elasticity, the alloy can be used to fabricate many types of medical implants including, but not limited to, hip joints, knee joints, cheek bones, tooth implants, skull plates, fracture plates, intramedullary rods, staples, bone screws, spinal implants, pelvic plates, and other implants.

Further, as mentioned before, the hot worked, high strength, low modulus alloy will find application in a multitude of uses ranging from aircraft assembly to golf clubs to fabrication of equipment for use in hot, corrosive environments, i.e. wherever a low modulus, high strength, corrosion resistant metal is needed.

BRIEF DESCRIPTION OF THE DRAWINGS

FIGS. 4A and 4B show the effect of various techniques of age hardening on two different invention alloys.

FIG. 5A is a schematic diagram of a side view of a typical intramedullary rod used in orthopedic applications.

FIG. 5B is a view of 5A, rotated by 90°.

FIG. 6A is a schematic diagram of a typical bone screw.

FIG. 6B is an end view of 6A.

FIG. 7 is a schematic diagram showing a typical screw for fixing bone plates.

FIG. 8 is a schematic diagram of a compression hip screw.

FIG. 9A is a side view of a typical bone plate, in partial cross-section, for securing to the hip.

FIG. 9B is the plate of 9A rotated by 90° to show 6 holes for bone screws to affix the plate in the body and a topmost hole for receiving a compression hip screw, like that of FIG. 8.

FIG. 9C is a cross-sectional view of 9B taken at 9C—9C.

DETAILED DESCRIPTION OF THE PREFERRED EMBODIMENTS

The inventive alloy implants may be produced by combining, as commercially pure components, titanium, niobium and optionally zirconium in the appropriate proportions, heating the alloy to above its β-transus (or within the range of temperatures below and within about 100° C. of the β-transus), hot working, rapidly cooling to about room temperature, and aging the alloy at temperatures below the β-transus for a sufficient length of time to allow strength development. It is essential that cooling be carried out rapidly, as by quenching with water. Conventional convective air cooling is not sufficiently rapid to produce the high strength, low modulus alloy of the invention after aging.

Figure 1A:
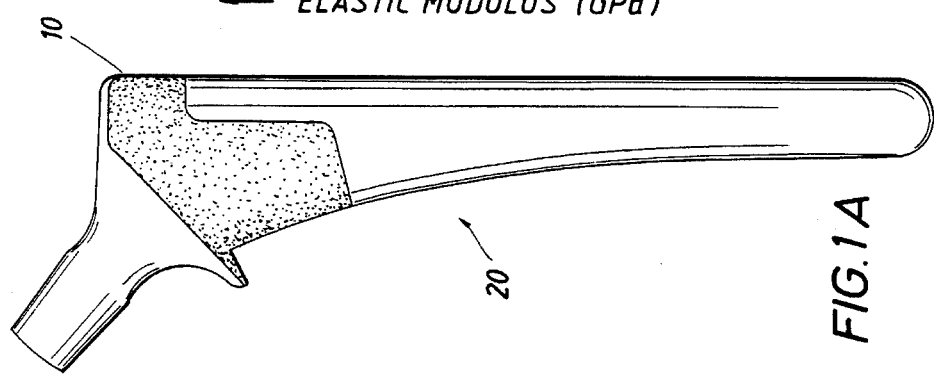
FIG. 1A is a schematic diagram of a hip joint prosthesis with a porous coating.
Figure 1B:
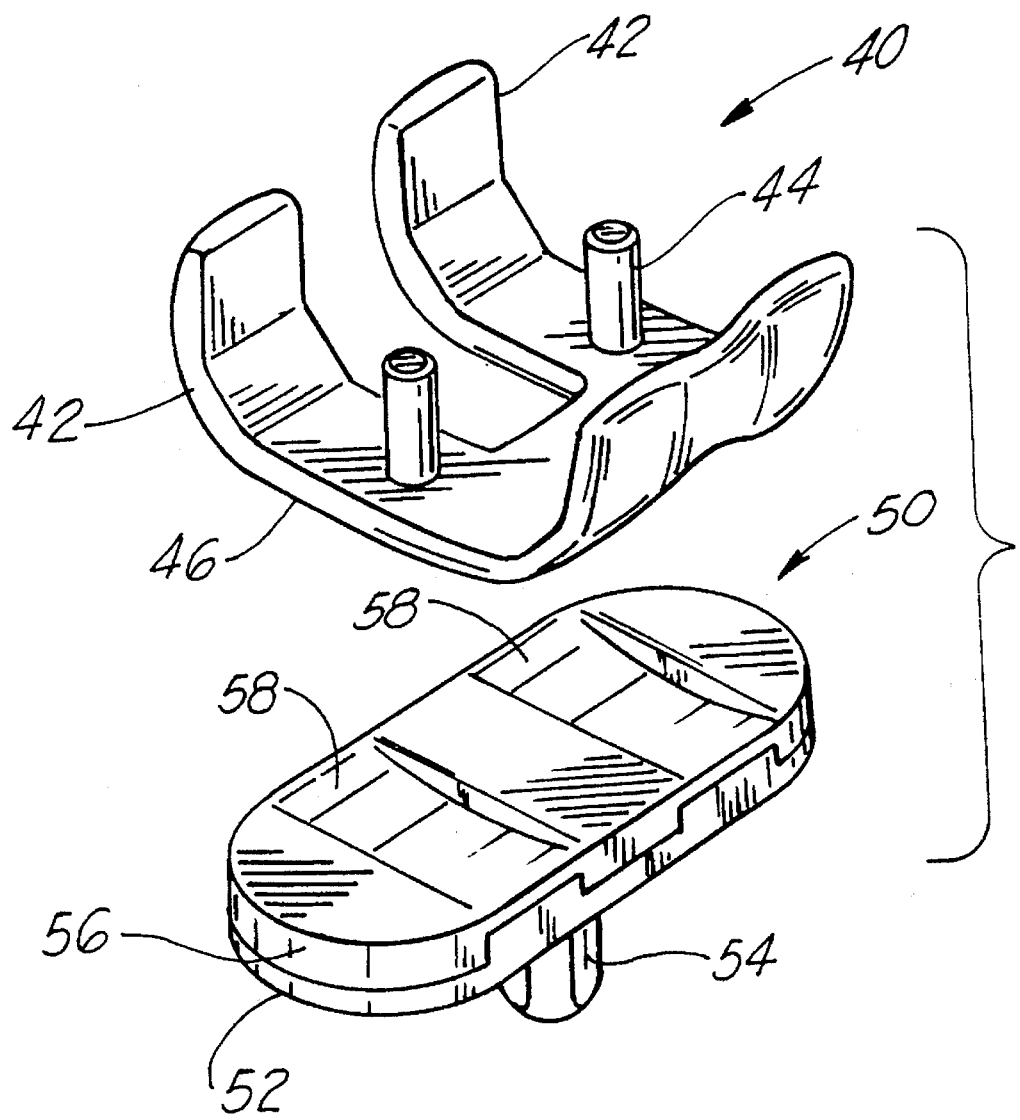
FIG. 1B is a schematic diagram of a modular knee joint prosthesis.

The titanium alloys are useful in the manufacture of medical implants, especially orthopedic implants, and possess the characteristics of high strength, low modulus of elasticity, corrosion resistance to body fluids and tissue, and are free from any potentially toxic elements. Thus, the alloys are especially useful in the fabrication of hip stem implants (FIG. 1A) bone plates (FIGS. 9A, B, C), intramedullary rods (FIGS. 5A, B), compression hip screws (FIG. 8), spinal implants, modular knee joints (FIG. 1B), and the like. Typical modular knee joints as shown in FIG. 1B include a femoral component 40 and a tibial component 50. The femoral component includes condyles 42 which provide articulating surfaces and pegs 44 for affixing to the femur. The tibial component 50 includes a tibial base 52 with a peg 54 for mounting the base onto the tibia. A tibial platform 56 is mounted atop the tibial base 52 and is supplied with grooves 58 that cooperate with the condyles 42. The tibial platform 56 is frequently made of an organic polymer (such as ultra-high molecular weight polyethylene) but the tibial base 52 and femoral component 40 are fabricated of metal. The invention provides tibial bases and femoral components of the above-described titanium-niobium-zirconium alloys.

The preferred titanium alloys include: (1) from about 10 to about 20 wt. % niobium or from about 35 to about 50 wt. % niobium, and (2) optionally up to 20 wt. % zirconium.

The most preferred inventive alloy contains titanium as the major component comprising about 74 wt. % of the alloy in combination with about 13 wt. % of zirconium and 13 wt. % of niobium.

While tantalum may be substituted for niobium to stabilize the β-phase titanium, niobium is the preferred component due to its effect of lowering the elastic modulus of the alloy when present in certain specific proportions. Other elements are not deliberately added to the alloy but may be present in such quantities that occur as impurities in the commercially pure titanium, zirconium, niobium or tantalum used to prepare the alloy and such contaminants as may arise from the melting (alloying) process. Filler materials, such as non-toxic tantalum, could also be added to reduce the β-transus (stabilize β) and improve strength as long as the relatively low modulus of elasticity (less than about 90 GPa) of the base alloy is not significantly affected.

Based upon the foregoing, it is apparent that the titanium proportion of certain embodiments of the invention alloy could be less than 50 wt. %. Nevertheless, these alloys are, for purposes of the specification and claims, referred to as "titanium alloys." For example, a titanium alloy may contain 20 wt. % zirconium and 45 wt. % niobium with only 35 wt. % titanium.

While the as-cast or powder metallurgically prepared alloy can be used as an implant material or for other applications, it can optionally be mechanically hot worked at 600°–950° C. The hot working process may include such operations as extrusion, hammer forging, bending, press forging, upsetting, hot rolling, swagging, and the like. After the final hot working step, the alloy should be cooled rapidly, as for instance, by water quenching. Slower rates of cooling, as by air convection cooling, are not recommended and are not effective in producing the high strength, low modulus alloy suitable for use as a medical implant. After cooling, it can then be reheated, preferably gradually over a period from about 0.5 to 10 hours, more preferably 1.5 to 5 hours to a maximum temperature of about 700° C., preferably about 500° C. Then, the implant material is maintained at this temperature for from about 0.25 to 20 hours, preferably for from about 2 to about 8 hours, more preferably for about 6 hours. This process, by a phenomenon called precipitation strengthening, is responsible for the high strength of the alloy in the hot worked, quenched and aged condition described above.

In the specification and claims, the term "high strength" refers to a tensile strength above about 700 MPa, preferably above about 800 MPa.

The term "low modulus" as used in the specification and claims refers to a Young's modulus below about 90 GPa.

Figure 2:
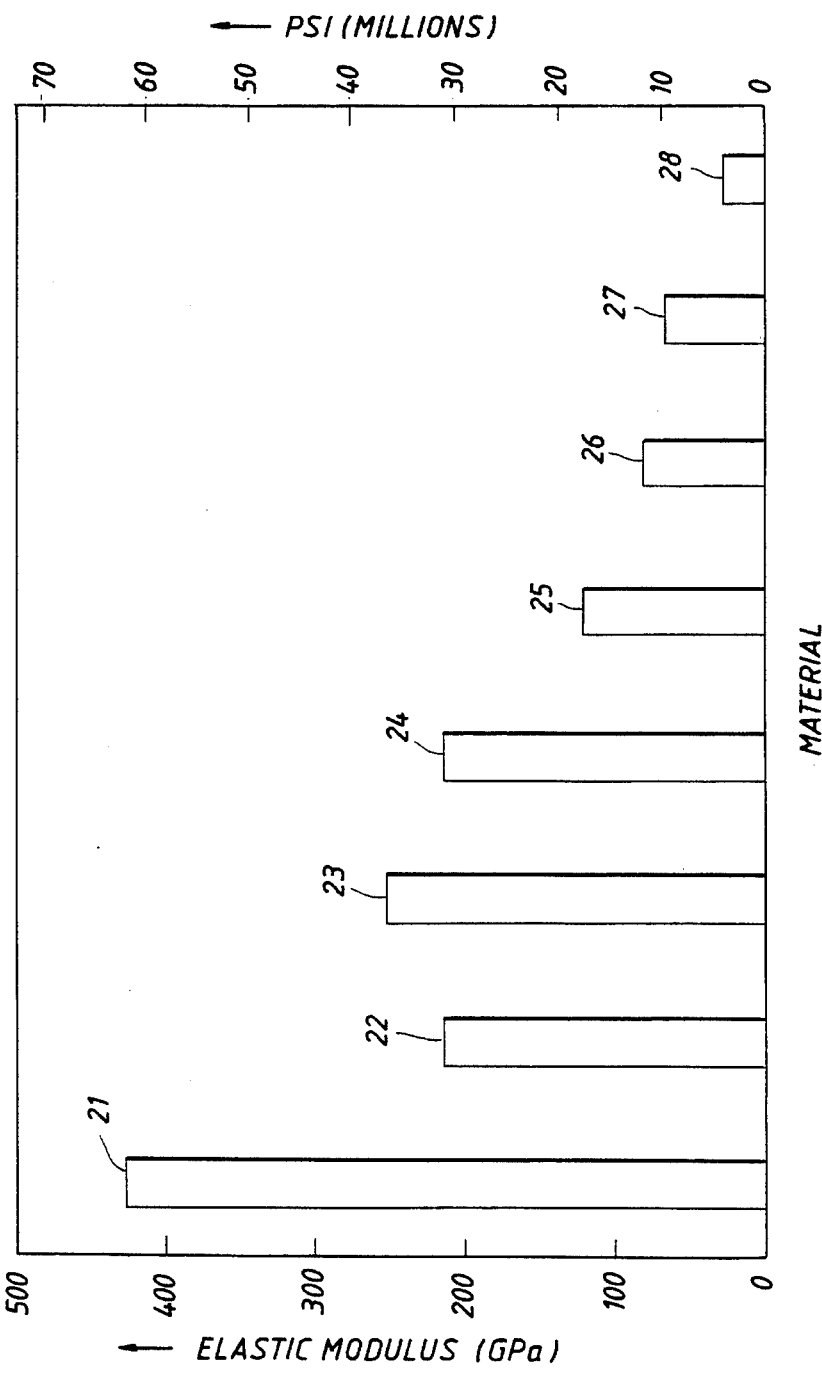
FIG. 2 is a bar graph comparing the elastic modulus of an invention alloy with other materials and bone.

A comparison of the mechanical properties of the invention's preferred Ti—13Zr—13Nb alloy with other implant materials is shown in FIG. 2 where the elastic modulus of alumina is represented by the bar marked 21, zirconia by 22, cobalt-chrome-molybdenum by 23, 316 stainless steel by 24, Ti—6A1—4V by 25, the invention Ti—13Zr—13Nb by 26, a composite of polyetheretherketone and carbon fiber by 27, and cortical bone by 28. Further, the strength of the invention alloy implants are compared with other alloys in FIG. 3 where Ti—6A-14V is represented by 29, 316 stainless steel (30% CW) by 30, cast cobalt-chrome-molybdenum by 31, 316 stainless steel by 32, Ti—13Zr—13Nb by 33, a composite of polyetheretherketone and carbon by 34, a carbon polysulfone composite by 35, and cortical bone by 36.

In titanium alloys, the niobium (or tantalum, if this element is added) acts to stabilize the β-phase since it is a β-isomorphous phase stabilizer. This results in a lower β-phase transus temperature and improved hot workability.

Niobium, in particular, when present in preferred quantities of from about 6 to about 10 atomic percent (most preferably about 8 atomic percent) or in an alternative preferred range of from about 22 to 32 atomic percent, produces a low modulus composition when alloyed with titanium. Deviation from these ranges of niobium concentration tends to increase the elastic modulus. In weight percent terms, these preferred compositional ranges of niobium in the titaniumzirconium alloy translate to about 10 to about 20 wt. % and about 35 to about 50 wt. %.

Titanium alloys containing about 13 wt. % niobium correspond to those having about 8 atomic percent niobium. Thus, the Ti—13Nb—13Zr alloy is believed to identify an optimal low modulus, titanium alloy composition.

As previously mentioned, tantalum may be substituted for niobium to stabilize the β-phase, but niobium is preferred due to its effect in reducing the elastic modulus. Substitution with zirconium can improve strength.

Whereas the niobium proportion is critical to obtain the desired low modulus property, the zirconium proportion is not as critical. It is desirable to maintain the proportion of zirconium at less than about 20 wt. % but higher proportions are also useful.

Zirconium, it is believed, is capable of stabilizing both α and β-phase titanium alloy, but acts by being in solution in the alloy as a β-stabilizer by slowing the transformation process in the inventive alloy. It is further believed that the larger ionic radius of zirconium (35% larger than that of titanium) helps to disrupt ionic bonding forces in the alloy resulting in some reduction in the modulus of elasticity.

In order to effect the transition to the β-phase (which is not essential to produce the high strength, low modulus alloy implants of the invention), the alloy may be treated by heating to above the β-transus temperature, e.g., to about 875° C., for about 20 minutes. Lower temperatures above the β-transus may also be used. The β-phase may also be induced by heating to higher temperatures for shorter periods of time. The critical factor for transition to the β-phase is heating to at least about the β-transition temperature, which is about 728° C. for Ti—13Zr—13Nb, for. a period of time sufficient to obtain a substantial conversion of the titanium alloy to the β-phase prior to cooling to room temperature. Conversion of the alloy to the β-phase and cooling may be effected before during, or after shaping for implantation and sintering of a porous metal coating, whichever is most convenient.

It should be noted that heating to above the β-transus and hot working at such elevated temperature while converting most or all of the alloy to the β-phase, is not essential to obtain the desired high strength and low modulus. Indeed, the alloy may be heated to a temperature as low as about 100° C. below the β-transus, and hot worked at this lower temperature to achieve high strength and low modulus, after rapid quenching and aging, without complete transformation to the β-phase. The region immediately below the β-transus temperature is called the α+β region. Hot working may be performed after heating to this α+β region and, possibly, even temperatures below this region, i.e., temperatures as low as about 100° C. below the β-transus.

The effect of hardness and aging conditions for Ti—13Zr—13Nb and Ti—18Zr—6Nb alloys, cooled at two different rates from above the β-transus, are shown in FIGS. 4A(1) and 4B(2). In FIGS. 4A(1) and 4A(2), a water quench is used whereas in FIGS. 4B(1) and 4B(2), air cooling is used.

The β-transus temperature of the most preferred Ti—13Nb—13Zr alloy is about 728° C. The alloy may be heated to above the β-transus, e.g., about 800° C., for forging. Other intermediate temperatures may also be used, but at temperatures lower than about 600° C. forging may be difficult because of the poorer formability of the alloy at these low temperatures.

The machining, casting or forging of the alloy into the desired implant shape may be carried out by any of the conventional methods used for titanium alloys. Further, implants could be pressed from the powdered alloy under conditions of heat and pressure in pre-forms in the shape of the desired implant. Conventional sintering and hot isostatic pressure treatments can be applied.

While the alloy provides a non-toxic prosthesis material, it may yet be desirable for other reasons, such as microfretting against bone or polyethylene bearing surfaces, to coat the metal surface. In this event, the surface may be coated with an amorphous diamond-like carbon coating or ceramic-like coating such as titanium nitride or titanium carbide, or the oxide, nitride or carbide of zirconium, using chemical or plasma vapor deposition techniques to provide a hard, impervious, smooth surface coating. Alternatively, a coating may be formed in situ on the shaped alloy by exposure to air, oxygen, and/or nitrogen at elevated temperatures to oxidize or nitride the surface of the alloy to a desired depth. Typically these coatings, resulting from the diffusion of oxygen or nitrogen into the metal surface, are up to about 100μ thick or greater. These in situ coatings are tightly adherent and more wear resistant than the metallic alloy surface. Coatings are therefore especially useful if the alloy is subjected to conditions of wear, such as, for instance, in the case of bearing surfaces of knee or hip prostheses.

Methods for providing hard, low-friction, impervious, biocompatible amorphous diamond-like carbon coatings are known in the art and are disclosed in, for example, EPO patent application 302 717 A1 to Ion Tech and Chemical Abstract 43655P, Vol. 101 describing Japan Kokai 59/851 to Sumitomo Electric, all of which are incorporated by reference herein as though fully set forth.

Further, the metal alloys may be hardened by interstitial ion implantation wherein the metal surface is bombarded with the ions of oxygen or nitrogen, and the like. The metal retains a metallic-appearing surface but the surface is hardened to a depth of about 0.1μ. The metals may also be surface hardened by internal oxidation, as described in our copending U.S. Ser. No. 832,735, filed Feb. 7, 1992.

Implants fabricated from the inventive alloy may be supplied with a porous bead, powder, or wire coating of titanium alloy of the same or different composition including pure titanium to allow stabilization of the implant in the skeletal structure of the patient after implantation, by bone ingrowth into the porous structure. Such porous structures are sometimes attached to the implant surface by sintering. This involves heating the implant to above about 1250° C. The mechanical properties of titanium alloys can change significantly due to substantial grain growth and other metallurgical factors arising from the sintering process. Thus, after sintering to attach the porous coating, it is preferred that the Ti—13Zr—13Nb implant be reheated to about 875° C. (or above the β-transus) for 20–40 minutes then quenched before being aged at about 500° C. for about 6 hours to restore mechanical properties. If quenched adequately from the sintering temperature, it may be possible to go directly to the aging process.

The following examples are intended to illustrate the invention as described above and claimed hereafter and are not intended to limit the scope of the invention in any way. The aging temperature used in the examples is determined to be acceptable, although not necessarily optimal.

EXAMPLE 1

An alloy including, by weight, 74% titanium, 13% niobium and 13% zirconium, was hot rolled at a temperature in the range 825°–875° C. to 14 mm thick plate. The plate was cooled to room temperature then reheated to 875° C. where it was maintained for 20 minutes and then water quenched to room temperature. The β-transus for this alloy was about 728° C. as compared to about 1000° C. for Ti—6A1—V. The mechanical properties of the heat-treated, quenched Ti—Zr—Nb alloy, which has an acicular transformed β-structure, are shown in Table I.

TABLE I

Mechanical Properties of Ti—13Zr—13Nb
As Water Quenched from above B-Transus Temperature

| | |
|---|---|
| Tensile Strength | 710 MPa |
| Yield Strength | 476 MPa |
| Elongation | 26% |
| Reduction in Area | 70% |
| Young's Modulus | 62 GPa |
| Rockwell C Hardness | 18–19 |

EXAMPLE 2

The heat-treated, quenched Ti—Zr—Nb alloy of Example 1 was aged by heating at 500° C. for 6 hours. The mechanical properties of this aged alloy are shown in Table II.

TABLE II

Mechanical Properties of Quenched
Ti—13Zr—13Nb Aged 500° C. for Six Hours

| | |
|---|---|
| Tensile Strength | 917 MPa |
| Yield Strength | 796 MPa |
| Elongation | 13% |
| Reduction in Area | 42% |
| Young's Modulus | 76.6 GPa |
| Rockwell C Hardness | About 29 |

EXAMPLE 3

Samples of the alloy of Example 1 were sintered at about 1250° C. to attach a porous titanium bead coating of the type shown in FIG. 1. The bead-coated alloy samples were then reheated to 875° C. and maintained at this temperature for 40 minutes before being waterquenched. A group of six samples were aged at 500° C. for 6 hours and the mechanical properties of aged and non-aged samples (three each) were tested and are shown in Table III.

TABLE III

Mechanical Properties of Ti—13Zr—13Nb Alloy
Following Bead Sintering, Reheating to
875° C., and Water Quenched

| | As-Quenched (Avg.) | Aged (500° C. Six Hours) |
|---|---|---|
| Tensile Strength | 664 MPa | 900 MPa |
| Yield Strength | 465 MPa | 795 MPa |
| Elongation | 20% | 4% |
| Reduction Area | 46% | 9% |
| Young's Modulus | 61.8% GPa | 74.7 GPa |

Note that the sintering treatment can significantly alter the mechanical properties, particularly ductility. Thus, an alloy acceptable for a particular application in unsintered form may not necessarily be effective in that application following a high-temperature sintering treatment often used to attach a porous titanium coating. To minimize these effects, lower temperature diffusion bonding methods can be used in which a temperature near the β-transus may be effective. Alternatively, pre-sintered porous metal pads can be tack-welded to the implant. Yet another alternative is to apply the porous coating by a plasma-spraying method which does not expose the bulk of the material to high temperature.

EXAMPLE 4

Figure 3:
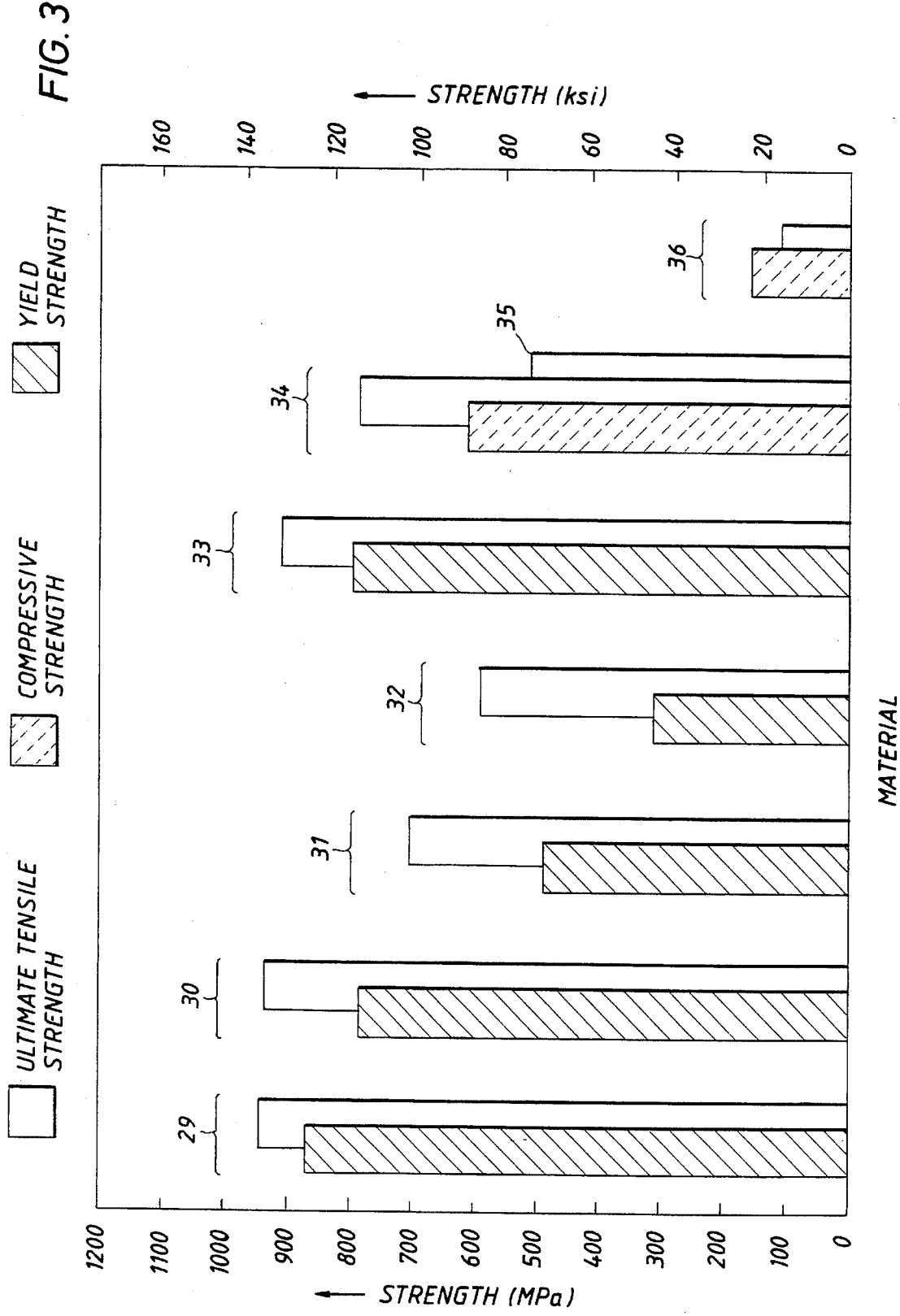
FIG. 3 is a bar graph comparing the strength of an invention alloy with other materials and bone.

A comparison of the elastic modulus, tensile strength and yield strength of the Ti—13Zr—13Nb invention alloy with those of known alloys, composites and cortical bone, are summarized in FIGS. 2 and 3. $Al_2O_3$ and $ZrO_2$ refer to ceramics while C/PEEK refers to carbon reinforced polyetheretherketone composite and C/PS refers to a carbon reinforced polysulfone composite. All the mechanical property data of FIGS. 2 and 3 were obtained from literature sources except for the data pertaining to the invention alloy which were measured using standard ASTM tensile testing techniques. It is significant that the Ti—13Zr—13Nb invention alloy has an elastic modulus similar to carbon fiber reinforced composites and closer to that of bone than the other metals (FIG. 2) while at the same time possessing a strength comparable to or better than other metals (FIG. 3).

EXAMPLE 5

A sample of Ti—18Zr—6Nb was sintered to attach a porous metal coating. Thereafter, the sintered alloy was reheated to 875° C., i.e. above the β-transus, and water quenched. The properties of the as-quenched alloy are shown in Table IV. The sample was then aged at 450° C. for 3 hours and tested. These results are also shown in Table IV.

As compared to the Ti—13Zr—13Nb alloy of Example 3, this alloy's modulus of elasticity is not as low but is still lower than that of Ti—6A1—4V. Further, the Ti—18Zr—6Nb alloy has a relatively low β-transus, about 760° C. compared to that of Ti—6A1-4V which is about 1000° C.

TABLE IV

Mechanical Properties of Ti—18Zr—6Nb Following A
High Temperature Sintering Treatment, Reheating to
875° C., and Water Quenching and Aging

| | As-Quenched | Aged 450° C., 3 Hrs. |
|---|---|---|
| Tensile Strength | 807 MPa | 876 MPa |
| Yield Strength | 659 MPa | 733 MPa |

TABLE IV-continued

Mechanical Properties of Ti—18Zr—6Nb Following A
High Temperature Sintering Treatment, Reheating to
875° C., and Water Quenching and Aging

|  | As-Quenched | Aged 450° C., 3 Hrs. |
|---|---|---|
| Elongation | 8% | 8% |
| Reduction in Area | 26% | 28% |
| Elastic Modulus | 85.2 GPa | 86.8 GPa |

Note that because of the less than optimum niobium content, the elastic modulus is not as low as the previous example. Thus, proper selection of niobium content is important for optimizing the low elastic modulus. However, the presence of zirconium helps to keep the elastic modulus at an acceptably low level (less than about 90 GPa).

EXAMPLE 6

The effect of aging conditions on Ti—13Zr—13Nb and Ti—18Zr—6Nb was investigated. Separate samples of each alloy were air-cooled or water-quenched from above the β-transus, aged at 500°, 450°, 400° and 350° C. for up to 6 hours then air cooled. The results are recorded in FIG. 4.

EXAMPLE 7

Forgings of Ti—13Nb—13Zr were prepared at temperatures of 800° and 680° C. These forgings were either water quenched or air cooled from the forging temperature and their mechanical properties were determined:

TABLE V

| Forging Temp. °C. | 800 | 800 | 680 | 680 | 800* |
|---|---|---|---|---|---|
| Quench medium | Air | Water | Air | Water | Water |
| Ultimate Tensile Strength, MPa | 789 | 765 | 852 | 762 | 691 |
| Yield Strength, MPa | 592 | 518 | 700 | 517 | 444 |
| Elongation, % | 21 | 23 | 18 | 27 | 28 |
| Reduction in Area, % | 72 | 60 | 72 | 73 | 72 |
| Young's Modulus, GPa | 84 | 66 | 85 | 72 | 60 |
| Hardness, Rockwell C | 20 | 26 | 27 | 25 | — |

*Net-shape forged

Forgings of 19 mm minimum diameter Ti—13Nb—13Zr, which had been air cooled after forging, were heat treated by aging at 350° to 500° C. for from 1.5 to 6 hours. The mechanical properties of these forgings were as follows:

TABLE VA

| Forging Temp., °C. | 800 | 800 | 800 | 800 |
|---|---|---|---|---|
| Aging Temp., °C. | 500 | 450 | 350 | 350 |
| Aging Time, hrs. | 6 | 1.5 | 6 | 1.5 |
| Ultimate Tensile Strength, MPa | 775 | 810 | 872 | 882 |
| Yield Strength, MPa | 651 | 625 | 641 | 639 |
| Elongation, % | 23 | 20 | 18 | 17 |
| Reduction in Area, % | 74 | 70 | 60 | 59 |
| Young's Modulus, GPa | 86 | 84 | 88 | 87 |

The strength of these alloys is not very high, even after aging, since they had been air cooled (slow cooling as opposed to rapid cooling of water quenching) after forging.

Other Ti—13Nb—13Zr forgings, also of minimum 19 mm diameter, were water quenched after forging, then heat treated. The mechanical properties of these forgings are recorded in Table VI.

TABLE VI

| Forging Temp., °C. | 800 | 800 | 800 | 800 | 800 | 800 | 800 | 680 | 680 | 680 |
|---|---|---|---|---|---|---|---|---|---|---|
| Quench[1] | 3 | 1 | 2 | 2 | 3 | 2 | 2 | 1 | 1 | 1 |
| Aging Temp., °C. | 500 | 500 | 500 | 500 | 500 | 450 | 400 | 500 | 450 | 400 |
| Aging Time, hrs | 0.5 | 1 | 2 | 4 | 6 | 2 | 4.3 | 2 | 2 | 2 |
| Ultimate Tensile Strength, MPa | 983 | 1036 | 985 | 999 | 1027 | 978 | 994 | 983 | 1082 | 1063 |
| Yield Strength, MPa | 854 | 912 | 872 | 865 | 916 | 831 | 831 | 852 | 859 | 852 |
| Elongation, % | 11 | 11 | 12 | 14 | 12 | 10 | 9 | 15 | 10 | 10 |
| Reduction in Area, % | 42 | 41 | 48 | 48 | 43 | 37 | 27 | 61 | 35 | 33 |
| Young's Modulus, GPa | 75 | 80 | 81 | 81 | 82 | 74 | 74 | 88 | 88 | 84 |
| Hardness, Rockwell C | 35 | 32 | 33 | 33 | 31 | 32 | 36 | 32 | 35 | 36 |

[1] 1 = water quenched only after final forging step.
2 = water quenched only after last two forging steps.
3 = water quenched after all three forging steps.

The alloy shows significant further improvement in strength while retaining a Young's modulus in the range 74–90 GPa. Hardness is also significantly greater than for the non-heat treated alloy as well as the reheated, quenched, and aged alloy of Example 2.

EXAMPLE 8

Several tests were performed to determine the effect on the physical properties of Ti—13Zr—13Nb when forged at different temperatures, aged at different temperatures for periods of time, and quenched under different conditions.

Water quenched 19 mm minimum diameter samples from hip stems (proximal, mid, or distal sections) were heat treated at low temperatures for short times and their properties measured and recorded in Table VII.

TABLE VII

| Forging Temp., °C. | 800 | | | 800 | | | 800 | | | 800 | |
|---|---|---|---|---|---|---|---|---|---|---|---|
| Quench[2] | 3 | | | 2 | | | 2 | | | 1 | |
| Aging Temp., °C. | 500 | | | 450 | | | 400 | | | 450 | |
| Aging Tim, hrs. | 0.5 | | | 2 | | | 4.3 | | | 2 | |
| Part of Stem[1] | P | M | D | P | M | D | P | M | D | P | D |
| Ultimate Tensile Strength, MPa | 1047 | 992 | 909 | 1061 | 985 | 889 | 1082 | 937 | 965 | 1109 | 1006 |
| Yield Strength, MPa | 930 | 875 | 758 | 930 | 834 | 730 | 923 | 765 | 806 | 978 | 861 |
| Elongation, % | 10 | 12 | 12 | 9 | 8 | 14 | 8 | 10 | 8 | 11 | 10 |
| Reduction in Area, % | 40 | 45 | 42 | 36 | 27 | 49 | 25 | 29 | 27 | 37 | 34 |
| Young's Modulus, GPa | 80 | 76 | 70 | 76 | 75 | 71 | 77 | 72 | 73 | 80 | 77 |

[1]P = proximal part of stem.
M = mid-stem region.
D = distal end of stem.
[2]1 = water quench after final forging only.
2 = water quench after last two forging steps only.
3 = water quench after all three forging steps.

Forgings of 14 mm minimum diameter were water quenched after the final forging step only, then aged at 500° C. for 1,2 or 3 hours. Their properties were:

TABLE VIII

| Forgings Temp., °C. | 800 | 800 | 800 |
|---|---|---|---|
| Aging Temp., °C. | 500 | 500 | 500 |
| Aging Time, hr | 1 | 2 | 3 |
| Ultimate Tensile Strength, MPa | 953 | 960 | 1017 |
| Yield Strength, MPa | 802 | 811 | 898 |
| Elongation, % | 14 | 11 | 12 |
| Reduction in Area, % | 50 | 44 | 42 |
| Young's Modulus, GPa | 73 | 73 | 82 |

The forgings show an increase in both yield strength and tensile strength with time of aging.

TABLE IXA

| | Plate |
|---|---|
| Ultimate Tensile Strength (MPa) | 786 ± 0 |
| Yield Strength (MPa) | 539 ± 12 |
| Elongation (%) | 21 ± 0 |
| Reduction in Area (%) | 51 ± 5 |
| Young's Modulus (GPa) | 74 ± 3 |
| Hardness, Rockwell C | 24.6 ± 2.0 |

The hot worked and water quenched plate was then subjected to aging cycles consisting of a gradual heating up step and an isothermal aging step. The heating up appeared to produce a "preaging effect" on the material which enhanced subsequent aging response and produced a higher strength. The aging cycle included heating up the plate over a period of 1.5 to 5 hours up to 500° C. (preaging), followed by 6 hours of aging at 500° C. The resultant mechanical properties of the plate are shown in Table IXB:

TABLE IXB

| Ramp-up Time to 500° C. (hr): | 1.5 | 2 | 2.5 | 3 | 4 | 5 |
|---|---|---|---|---|---|---|
| Ultimate Tensile Strength (MPa) | 1016 ± 3 | 1020 ± 14 | 1016 ± 3 | 1020 ± 0 | 1034 ± 0 | 1037 ± 3 |
| Yield Strength (MPa) | 899 ± 3 | 899 ± 7 | 889 ± 9 | 903 ± 7 | 908 ± 3 | 910 ± 7 |
| Elongation (%) | 9 ± 1 | 9 ± 1 | 9 ± 1 | 10 ± 0 | 9 ± 1 | 8 ± 0 |
| Reduction in Area (%) | 26 ± 4 | 28 ± 5 | 30 ± 3 | 30 ± 1 | 28 ± 2 | 25 ± 2 |
| Young's Modulus (GPa) | 82.6 ± 1.5 | 81.2 ± 0.6 | 82.4 ± 1.5 | 83 ± 1.5 | 81.9 ± 1.4 | 81.6 ± 0.3 |
| Hardness, Rockwell C | — | — | 32.4 ± 1.6 | — | — | — |

EXAMPLE 9

A 12.5 inch long by 14 inch diameter segment was cut from an ingot of Ti—13Zr—13Nb which had been produced by arc melting. The plate was press forged to a 3 inch thickness at 1000° C. The press forged plate was then air annealed at 1100° C. for 15–30 minutes before being hot rolled at 900° C. to a 1.35 inch penultimate thickness. The hot rolled plate was then reheated to 900° C., hot rolled to 1.04 inch final thickness, and water quenched before being blasted and pickled. The mechanical properties of the plate were as follows:

From comparing Tables IXA and IXB, it is apparent that strength and hardness have increased significantly due to the aging process.

EXAMPLE 10

A 54 inch long by 14 inch diameter bar was cut from an ingot of Ti—13Zr—13Nb produced by arc melting. The bar was rotary forged to a 5.4 inch diameter at 875° C., then air annealed at 1050° C. for 3 hours. Thereafter, the bar was rotary forged at 800° C. to 2.5 inch diameter, and rotary swagged at 750° C. to 1.2 inch penultimate diameter. The swagged bar was then reheated to 925° C. before being rotary swagged to a 1 inch final diameter. The bar was water quenched, blasted and pickled, and then centerless ground.

The resultant mechanical properties of this Ti—13Zr—13Nb bar were as follows:

TABLE XA

|  | Bar |
| --- | --- |
| Ultimate Tensile Strength (MPa) | 722 ± 9 |
| Yield Strength (MPa) | 463 ± 10 |
| Elongation (%) | 26 ± 0 |
| Reduction in Area (%) | 66 ± 2 |
| Young's Modulus (GPa) | 79 ± 9 |
| Hardness, Rockwell C | 24 ± 2.7 |

The hot worked and water quenched bar was then subjected to aging cycles including a gradual heating up step and an isothermal aging step. Once again, the heating up appeared to produce a preaging effect on the bar, which enhanced subsequent aging response and produced a higher strength material. During aging, the bar was first gradually heated, over a period of 1.5 to about 5 hours, up to 500° C. This was followed by 6 hours of isothermal aging at 500° C. The resultant mechanical properties of the bar were as follows:

TABLE XB

| Ramp-up Time to 500° C. (hr): | 2.5 |
| --- | --- |
| Ultimate Tensile Strength (MPa) | 1008 ± 6 |
| Yield Strength (MPa) | 881 ± 13 |
| Elongation (%) | 10 ± 3 |
| Reduction in Area (A %) | 32 ± 14 |
| Young's Modulus (GPa) | 82.4 ± 2.3 |
| Hardness, Rockwell C | 31.5 ± 0.6 |

As can be seen from a comparison of Table XA and Table XB, the strength and hardness of the bar increased significantly as a result of the aging and preaging processes.

The invention has been described with reference to its preferred embodiments. From this description, a person of ordinary skill in the art may appreciate changes that could be made in the invention which do not depart from the scope and spirit of the invention as described above and claimed hereafter.

What is claimed is:

1. A biocompatible medical implant of low modulus and high strength for implantation into a recipient's body where it is subject to varying loads imposed by physical forces and corrosive effects of body fluids, said medical implant comprising:

a metallic alloy, said metallic alloy comprising a grain structure that results from said alloy having been subjected to metallurgical treatment steps comprising:

(i) heating to a temperature in the range of from 100° C. below a B-transus temperature of the alloy to above the β-transus temperature;

(ii) hot working the alloy to produce a hot worked alloy;

(iii) rapidly quenching the hot worked alloy; and (iv) aging the alloy at a temperature and for a time sufficient to develop strength in the alloy that is greater than an alloy of identical wt % composition that has not been subjected to said metallurgical treatment steps;

wherein the metallic alloy comprises as components: titanium; from about 10 to about 20 wt. % niobium; an amount of zirconium in solution in the alloy sufficient to act as a beta stabilizer by slowing the transformation of beta; and wherein the alloy is substantially free of toxic elements, said toxic elements being aluminum, vanadium, cobalt, nickel, molybdenum and chromium, except such amounts of said toxic elements as may occur as impurities in the components and contaminants as a result of processing, the amounts of said impurities and contaminants being insignificant to cause adverse effect on the recipient's body.

2. The medical implant of claim 1, wherein the step of heating comprises heating to above the β-transus temperature of the alloy.

3. The medical implant of claim 1, wherein the step of aging is at a temperature in the range from about 350° to about 550° C.

4. The medical implant of claim 3, wherein the aging is at a temperature of about 500° C. for about 6 hours.

5. The medical implant of claim 1, wherein the implant has a strength greater than about 800 MPa.

6. The medical implant of claim 1, further comprising an amount of tantalum sufficient to stabilize the β-phase without significantly increasing the modulus of elasticity of the implant.

7. The medical implant of claim 1, wherein the alloy consists essentially of: 74 wt. % titanium, 13 wt. % niobium, and 13 wt. % zirconium.

8. The medical implant of claim 1, wherein the implant is selected from the group consisting of bone plates, bone screws, intramedullary rods, and compression hip screws.

9. The medical implant of claim 8, further comprising a protective coating of amorphous diamond-like carbon on at least a portion of an outer surface of the implant.

10. The medical implant of claim 8, further comprising at least a partial outer surface protective coating selected from the group consisting of the oxides, nitrides, carbides, and carbonitrides of elements of the metal alloy.

11. The medical implant of claim 8, wherein the implant is internally oxidized or nitrided beneath outer surfaces of the implant to produce a hardened medical implant.

12. The medical implant of claim 1, wherein the implant is a hip joint system.

13. The medical implant of claim 12, wherein the alloy consists essentially of: 74 wt % titanium, 13 wt % zirconium and 13 wt % niobium.

14. The medical implant of claim 13, wherein the hip joint stem has a strength greater than about 800 MPa.

15. The medical implant of claim 12, further comprising a protective coating of amorphous diamond-like carbon on at least a portion of an outer surface of the implant.

16. The medical implant of claim 12, further comprising at least a partial outer surface protective coating selected from the group consisting of the oxides, nitrides, carbides, and carbonitrides of elements of the metal alloy.

17. The medical implant of claim 1, wherein the implant is selected from the components of a modular knee joint consisting of a femoral component and a tibial base component.

18. The medical implant of claim 17, wherein the implant is internally oxidized or nitrided beneath outer surfaces of the implant to produce a hardened medical implant.

19. The medical implant of claim 17, wherein the implant has a strength greater than about 800 MPa.

20. The medical implant of claim 17, further comprising a protective coating of amorphous diamond-like carbon on at least a portion of an outer surface of the implant.

21. The medical implant of claim 17, further comprising at least a partial outer surface protective coating selected from the group consisting of the oxides, nitrides, carbides, and carbonitrides of elements of the metal alloy.

22. The medical implant of claim 1, wherein the aging step comprises:

heating the rapidly quenched alloy to about 500° C. over a period of time from about 1.5 to about 5 hours; maintaining the gradually heated alloy at about 500° C. for about 2 to about 8 hours; and cooling the alloy to ambient conditions.

23. A biocompatible medical implant of low modulus and high strength for implantation into a recipient's body where it is subject to varying loads imposed by physical forces and corrosive effects of body fluids, said medical implant comprising:

a metallic alloy, said metallic alloy comprising a grain structure that results from said alloy having been subjected to metallurgical treatment steps comprising:
(i) heating to a temperature in the range from about 100° C. below a β-transus temperature of the alloy to above the β-transus temperature;
(ii) hot working the alloy to produce a hot worked alloy;
(iii) rapidly quenching the hot worked alloy; and
(iv) aging the alloy at about 500° C. for about six hours to develop strength in the alloy that is greater than an alloy of identical composition that has not been subjected to said metallurgical treatment steps and greater than about 800 MPa while maintaining modulus of elasticity at less than about 90 GPa;

wherein the metallic alloy comprises as components: about 74 wt. % titanium; about 13 wt. % niobium, and an amount of zirconium in solution in the alloy sufficient to act as a beta stabilizer by slowing the transformation of beta; and wherein the alloy is substantially free of toxic elements, said toxic elements being aluminum, vanadium, cobalt, nickel, molybdenum and chromium, except such amounts of said elements as may occur as impurities in the components and contaminants as a result of processing, the amounts of said impurities and contaminants being insignificant to cause adverse effect on the recipient's body.

24. The medical implant of claim 23, wherein the implant is selected from the group consisting of bone plates, bone screws, intramedullary rods, and compression hip screws.

25. The medical implant of claim 23, wherein the implant is a hip joint stem.

26. The medical implant of claim 23, wherein the implant is selected from the components of a modular knee joint consisting of a femoral component and a tibial base component.

27. The medical implant of claim 23, wherein the aging step comprises:
gradually heating the alloy over a period of from about 1.5 to about 5 hours to about 500° C., before the step of aging at about 500° C. for about 6 hours.

28. A biocompatible medical implant of low modulus and high strength for implantation into a recipient's body where the implant is subjected to varying loads imposed by physical forces and corrosive effects of body fluids, said medical implant comprising:

a metallic alloy, said metallic alloy comprising a grain structure that results from said alloy having been subjected to metallurgical treatment steps comprising:
(i) heating to a temperature in the range from about 100° C. below a β-transus temperature of the alloy to above the β-transus temperature;
(ii) hot working the alloy to produce a hot worked alloy;
(iii) rapidly quenching the hot worked alloy; and
(iv) aging the alloy by the steps comprising:
(a) heating to a temperature of about 500° C. over a period of from about 1.5 to about 5 hours;
(b) maintaining the alloy at the temperature of about 500° C. for about 2 to about 8 hours;
(c) cooling the alloy to ambient temperature conditions to develop strength in the alloy that is greater than an alloy of identical composition that has not been subjected to said metallurgical treatment steps;

wherein the metallic alloy comprises as components: titanium; from about 10 to about 20 wt. % niobium; and an amount of zirconium in solution in the alloy sufficient to act as a beta stabilizer by slowing the transformation of beta; and wherein the alloy is substantially free of toxic elements, said toxic elements being aluminum, vanadium, cobalt, nickel, molybdenum and chromium, except such amounts of said elements as may occur as impurities in the components and contaminants as a result of processing, the amounts of said impurities and contaminants being insignificant to cause adverse effect on the recipient's body.

29. The medical implant of claim 1 further comprising a surface with a porous coating for bone ingrowth into the implant.

30. The medical implant of claim 23 further comprising a surface with a porous coating for bone ingrowth into the implant.

31. The medical implant of claim 28 further comprising a surface with a porous coating for bone ingrowth into the implant.

32. The medical implant of claim 1 wherein at least a portion of the niobium is replaced with tantalum.

33. The medical implant of claim 23 wherein at least a portion of the niobium is replaced with tantalum.

34. The medical implant of claim 28 wherein at least a portion of the niobium is replaced with tantalum.

35. A biocompatible medical implant of low modulus and high strength for implantation into a recipient's body where it is subject to varying loads imposed by physical forces and corrosive effects of body fluids, said medical implant comprising:

a metallic alloy, said metallic alloy comprising a grain structure that results from said alloy having been subjected to metallurgical treatment steps comprising:
(i) heating to a temperature in the range of from about 100° C. below a β-transus temperature of the alloy to above the β-transus temperature;
(ii) hot working the alloy to produce a hot worked alloy;
(iii) rapidly quenching the hot worked alloy; and
(iv) aging the alloy at a temperature and for a time sufficient to develop strength in the alloy that is greater than an alloy of identical composition that has not been subjected to said metallurgical treatment steps;

wherein the metallic alloy comprises as components: titanium; from about 35 to about 50 wt. % niobium; and an amount of zirconium in solution in the alloy sufficient to act as a beta stabilizer by slowing the transformation of beta; and wherein the alloy is substantially free of toxic elements, said toxic elements being aluminum, vanadium, cobalt, nickel, molybdenum and chromium, except such amounts of said elements as may occur as impurities in the components and contaminants as a result of processing, the amounts of said impurities and contaminants being insignificant to cause adverse effect on the recipient's body.

36. A biocompatible medical implant of low modulus and high strength for implantation into a recipient's body where it is subject to varying loads imposed by physical forces and corrosive effects of body fluids, said medical implant comprising:

a metallic alloy, said metallic alloy comprising a grain structure that results from said alloy having been subjected to metallurgical treatment steps comprising:
   (i) heating to a temperature in the range from about 100° C. below a β-transus temperature of the alloy to above the β-transus temperature;
   (ii) hot working the alloy to produce a hot worked alloy;
   (iii) rapidly quenching the hot worked alloy; and
   (iv) aging the alloy at about 500° C. for about six hours to develop strength in the alloy that is greater than an alloy of identical composition that has not been subjected to said metallurgical treatment steps and greater than about 800 MPa while maintaining modulus of elasticity at less than about 90 GPa;

wherein the metallic alloy comprises as components: titanium; about 35 to about 50 wt. % niobium, and an amount of zirconium in solution in the alloy sufficient to act as a beta stabilizer by slowing the transformation of beta; and wherein the alloy is substantially free of toxic elements, said toxic elements being aluminum, vanadium, cobalt, nickel, molybdenum and chromium, except such amounts of said elements as may occur as impurities in the components and contaminants as a result of processing, the amounts of said impurities and contaminants being insignificant to cause adverse effect on the recipient's body.

37. A biocompatible medical implant of low modulus and high strength for implantation into a recipient's body where the implant is subjected to varying loads imposed by physical forces and corrosive effects of body fluids, said medical implant comprising:

a metallic alloy, said metallic alloy comprising a grain structure that results from said alloy having been subjected to metallurgical treatment steps comprising:
   (i) heating to a temperature in the range from about 100° C. below a β-transus temperature of the alloy to above the β-transus temperature;
   (ii) hot working the alloy to produce a hot worked alloy;
   (iii) rapidly quenching the hot worked alloy; and
   (iv) aging the alloy by the steps comprising:
      (a) heating to a temperature of about 500° C. over a period of from about 1.5 to about 5 hours;
      (b) maintaining the alloy at the temperature of about 500° C. for about 2 to about 8 hours;
      (c) cooling the alloy to ambient temperature conditions to develop strength in the alloy that is greater than an alloy of identical composition that has not been subjected to said metallurgical treatment steps;

wherein the metallic alloy comprises as components: titanium; from about 35 to about 50 wt. % niobium; and an amount of zirconium in solution in the alloy sufficient to act as a beta stabilizer by slowing the transformation of beta; and wherein the alloy is substantially free of toxic elements, said toxic elements being aluminum, vanadium, cobalt, nickel, molybdenum and chromium, except such amounts of said elements as may occur as impurities in the components and contaminants as a result of processing, the amounts of said impurities and contaminants being insignificant to cause adverse effect on the recipient's body.

38. The medical implant of claim 35 wherein at least a portion of the niobium is replaced with tantalum.

39. The medical implant of claim 36 wherein at least a portion of the niobium is replaced with tantalum.

40. The medical implant of claim 37 wherein at least a portion of the niobium is replaced with tantalum.

\* \* \* \* \*